(12) United States Patent
Yee et al.

(10) Patent No.: US 10,570,110 B2
(45) Date of Patent: Feb. 25, 2020

(54) SIMPLIFIED PROCESS TO EXTRACT QUASSINOIDS

(71) Applicant: University of the West Indies, Kingston (JM)

(72) Inventors: Trevor Herbert Yee, Kingston (JM); Helen Marjorie Jacobs, Kingston (JM)

(73) Assignee: University of The West Indies, St. Augustine (TT)

( * ) Notice: Subject to any disclaimer, the term of this patent is extended or adjusted under 35 U.S.C. 154(b) by 139 days.

(21) Appl. No.: 13/955,992

(22) Filed: Jul. 31, 2013

(65) Prior Publication Data

US 2014/0187799 A1  Jul. 3, 2014

Related U.S. Application Data

(63) Continuation of application No. PCT/IB2012/000372, filed on Feb. 1, 2012.

(60) Provisional application No. 61/438,395, filed on Feb. 1, 2011.

(51) Int. Cl.
| | | |
|---|---|---|
| *A61K 36/00* | (2006.01) | |
| *C07D 311/78* | (2006.01) | |
| *A61K 36/185* | (2006.01) | |
| *A61K 31/352* | (2006.01) | |
| *C07D 311/94* | (2006.01) | |

(52) U.S. Cl.
CPC .......... *C07D 311/78* (2013.01); *A61K 31/352* (2013.01); *A61K 36/185* (2013.01); *C07D 311/94* (2013.01); *A61K 2236/331* (2013.01); *A61K 2236/39* (2013.01)

(58) Field of Classification Search
None
See application file for complete search history.

(56) References Cited

U.S. PATENT DOCUMENTS

| | | | | |
|---|---|---|---|---|
| 8,568,794 | B2 * | 10/2013 | Diehl et al. | 424/725 |
| 2002/0019439 | A1 * | 2/2002 | Grieco et al. | 514/453 |
| 2006/0281808 | A1 * | 12/2006 | Yee et al. | 514/453 |
| 2008/0089958 | A1 * | 4/2008 | Diehl et al. | 424/725 |
| 2009/0171102 | A1 * | 7/2009 | Yee et al. | 549/278 |
| 2010/0221370 | A1 * | 9/2010 | Chan et al. | 424/769 |

OTHER PUBLICATIONS

Guo et al. (2009) Frontiers in Medicinal Chemistry, 4, 285-308.*
Web document entitled: "Simaroubaceae" (available at http://en.wikipedia.org/wiki/Simaroubaceae). Downloaded from website Feb. 24, 2015.*
Yang et al. (2004) Helvetica Chimica Acta vol. 87, 1591-1600.*
Raskin et al. (2004) Current Pharmaceutical Design 10, 3419-3429.*
Revilla et al. (1998) J. Agric. Food Chem. 46, 4592-4597.*
Cachet et al. (2009) Antimicrobial Agents and Chemotherapy, vol. 53, No. 10, 4393-4398. (Year: 2009).*
Garcia-Barrantes, et al. (2011) J. Ethnopharmacology, 134: 904-910. (Year: 2011).*
Toma, et al. (2002) Biol. Pharm. Bull. 25(9): 1151-1155. (Year: 2002).*
Toma et al. (2003) J. Ethnopharmacol. 85: 19-23. (Year: 2003).*
International Search Report and Written Opinion for International Application No. PCT/IB2012/000372 dated Jun. 22, 2012. 11 pages.
Tona, L. et al. "Antiamoebic and Phytochemical Screening of Some Congolese Medicinal Plants." Journal of Ethnopharmacology. Elsevier. Jan. 19, 1998, vol. 61, pp. 57-65.
Yang, Shen-Ping et al. "Five New Quassinoids from the Bark of Picrasma Quassioides." Helvetica Chimica Acta. No Month Listed 2004, vol. 87, pp. 1591-1600.
Mishra et al., "Plasmodium falciparum: in vitro interaction of quassin and neo-quassin with artesunate, a hemisuccinate derivative of artemisinin," Experimental Parasitology, Apr. 2010, vol. 124, No. 4, pp. 421-427.
Sarais et al., "Liquid chromatography electrospray ionization tandem mass spectrometric determination of quassin and neoquassin in fruits and vegetables," J. Agric. Food Chem., Mar. 10, 2010, vol. 58, No. 5, Abstract Only, 1 page.
Shields et al., "Inhibition of CYP1A1 by Quassinoids found in Picrasma excelsa," Planta Med., Feb. 2009, vol. 75, No. 2, Abstract Only, 1 page.

* cited by examiner

*Primary Examiner* — Russell G Fiebig
(74) *Attorney, Agent, or Firm* — Wilmer Cutler Pickering Hale and Dorr LLP

(57) ABSTRACT

Improved processes for the extraction of quassinoids such as quassin and neoquassin from natural substances containing these compounds are described. The process uses compounds that are Generally Recognized As Safe by the U.S. Food and Drug Administration. In a first embodiment, the process includes a sonication method using water and no organic solvent. The process is highly efficient and comprises fewer steps than other processes known in the art. In a second embodiment, a method of extracting quassinoids from natural substance comprising bark of a plant of the plant family Simaroubaceae is also disclosed. In a third embodiment, indirect sonication of quassinoids is described using a mixture of polar and non-polar organic solvents.

8 Claims, 7 Drawing Sheets

SIMPLIFIED PROCESS TO EXTRACT QUASSINOIDS

CROSS-REFERENCE TO RELATED APPLICATIONS

This application is a continuation of PCT Application No. IB2012/00372, filed on Feb. 1, 2012 which claims priority to U.S. Provisional Application No. 61/438,395, filed on Feb. 1, 2011, which is herein incorporated by reference in its entirety.

BACKGROUND

1. Field

This invention relates generally to an extraction process. More specifically, it is a process for the extraction of quassinoids from natural substances.

2. Background of the Invention

The Jamaican Quassia or Bitterwood, *Picrasma excelsa* is a member of the plant family Simaroubaceae in the order Sapindales. It is a tree, 6-25 meters tall, native to the Greater Antilles of the West Indies, and is common in various localities in Jamaica. See, Adams, C. D. Flowering Plants of Jamaica. 1972. University Press, Glasgow, p. 390. Other members of this family include, for example, *Quassia amara, Picrasma quassioides,* and *Quassia africana.*

Quassinoids have been indicated in the use of medicaments due to biological activities such as anti-malarial, anti-insecticidal, anti-amoebicidal, antileukemic, and anti-viral properties. See, for example, U.S. Pat. No. 5,639,712 to Grieco et al. Additionally, a new treatment for malaria has been proposed, using a combination of quassin/neoquassin with artesunate, a derivative of artemisinin (see Chakraborty, et al., Exp. Parisitol. 2010, 124 (4), 421-7, *Plasmodium falciparum*: in vitro interaction of quassin and neo-quassin with artesunate, a hemisuccinate derivative of artemesinin).

The main active ingredients of the wood, quassin and neoquassin (FIGS. 1A and 1B) have been reported to stimulate the appetite and to aid digestion; and because of these properties they are ingredients of aperitifs, and are also used in the treatment of the eating disorder, anorexia nervosa. See for example, Bown, D. The Royal Horticultural Society Encyclopedia of Herbs and Their Uses., 1995, Dorling Kindersley, London, p. 327; and Chavalier, A. The Dorling Kindersley Encyclopedia of Herbal Medicine. 2000. Dorling Kindersley, p. 247.

Additionally, quassin and neoquassin are used in alcoholic beverages, e.g. aperitifs such as Campari™, and other beverages and grapefruit flavored drinks, such as Ting™. See for example, Coyle, L. P. The World Encyclopedia of Foods. Facts On File, Inc., New York, 1982, p. 543. In addition, quassin and neoquassin have been used as natural botanical pesticides, against insects, nematodes, as a vermifuge, and as a treatment for head lice. See, Jacobson, M. 1989, Botanical Pesticides: Past, Present, and Future, American Chemical Society; Prakash, A., Rao, J. 1997, Botanical Pesticides in Agriculture. CRC Press Inc., Boca Raton, USA., pp. 254-255; Kuriyama, T., Ju, X., Fusazaki, S., Hishinuma, H., Satou, T., Koike, K., Nikaido, T., Ozoe, Y. 2005; Nematocidal quassinoids and bicyclophosphorothionates: a possible common mode of action on the GABA receptor, Pesticide Biochemistry and Physiology, 81, pp. 176-187; Chilemi, S., Chilemi, M. 2007, The Complete Herbal Guide: A Natural Approach to Healing the Body. Lulu Press, Inc., Raleigh, N.C., pp. 336-337; Munro, D., Munro, J., Bone, K. Head Lice Formulation, U.S. Patent Appl. No. 2004/0005344. Furthermore, they have also been formulated in a topical and intravaginal treatment for microbes and parasites (Diehl et al., Topical and Intravaginal Microbicidal and Antiparasitic Compositions Comprising Quassinoids or Quassinoid-Containing Plant Extracts, U.S. Patent Appl. No. 2008/0089958).

Jamaica is the most important global source of the Bitterwood wood chips, and some trade information on the export of wood chips from the island is given in Table 1.

TABLE 1

Exports of Bitterwood chips.*

| Year | Quantity (Kg) | Value (US$) |
|------|---------------|-------------|
| 2002 | 114,135 | 150,790 |
| 2003 | 89,825 | 141,643 |
| 2004 | 136,950 | 252,533 |
| 2005 | 105,317 | 147,207 |
| 2006 | 127,844 | 206,631 |
| 2007 | 107,139 | 175,207 |
| 2008 | 172,502 | 309,714 |

*Source: The Jamaica Export Trading Co., Ltd.

SUMMARY

An efficient process to produce quassinoids such as quassin and/or neoquassin in crystalline form is described, affording the marketing of a purified end product. In other aspects, a process to extract the quassinoids from the bark in order to utilize the tree more fully is described, especially since the tree is listed in the International Union of Conservation of Nature and Natural Resources' (IUCN) Red List of Threatened Species (see: The IUCN Red List of Threatened Species™, http://www.redlist.org/). The development of such a process would also lead to the possibility of local processing with the economic benefits of exporting a value added product and providing local employment. In still another aspect, a method of extracting quassinoids from natural substances using indirect sonication is described. The use of indirect sonication further simplifies the extraction process, which may eliminate the step of aqueous phase-organic phase partition. In some embodiments, quassinoids with high purity are directly crystallized from the extraction organic solvent, thus providing a highly simplified method for extracting quassinoids.

Disclosed herein is a highly efficient method for extracting one or more quassinoids from a natural substance. The method comprises applying an ultrasonic energy to a mixture of the natural substance with water to provide an aqueous phase of the quassinoids and extracting the aqueous phase with a water-immiscible organic solvent.

The bark of the plant *Picrasma excelsa* also contains quassinoids, as indicated by its bitter taste. However, extraction of quassinoids from the bark usually results in a dark colored extract, which is rich in impurities such as tannins and other polar compounds, rendering it unsuitable as a commercial product. As a result, in the harvesting of Bitterwood, Picrasma excelsa, the bark of the tree is usually discarded as a waste material and only the heartwood of the plant is prepared as chips for the export trade. Thus, tons of bark of Bitterwood rich in quassinoids are discarded annually. For a more economical utilization of the natural resources, also disclosed herein is an extraction method to extract quassinoids from natural substance including bark of a tree containing quassinoids, which results in efficient use of the natural resources.

An extraction method to extract quassinoids from natural substance including bark and heartwood of a tree containing quassinoids is disclosed. In some embodiments. the natural substance includes bark of the tree. In some embodiments, the natural substance includes the heartwood of the tree. In some embodiments. the natural substance includes bark and heartwood in their naturally-occurring ratios in a tree.

In one aspect, a method of processing quassinoid from natural substance containing the quassinoid is provided, including:
(a) providing a first mixture comprising natural substance comprising quassinoid and water, wherein the first mixture is free of organic solvent;
(b) applying ultrasonic energy to the first mixture to provide a first aqueous phase comprising quassinoid and a first spent natural substance containing less quassinoid than the natural substance; and
(c) extracting the quassinoid from the first aqueous phase with a first water-immiscible organic solvent to yield a first organic phase containing the quassinoid,
wherein the natural substance is a plant of the plant family Simaroubaceae or a portion thereof.

In any of the preceding embodiments, the method further includes:
d) providing a second mixture comprising first spent natural substance and water, wherein the second mixture is free of organic solvent;
(e) applying ultrasonic energy directly to the second mixture to provide a second aqueous phase comprising the quassinoid and a second spent natural substance containing less quassinoid than the first spent natural substance; and
(f) extracting the quassinoid from the second aqueous phase with a second water-immiscible organic solvent to yield a second organic phase containing the quassinoid.

In any of the preceding embodiments, the one or more quassinoids include quassin and/or neoquassin.

In any of the preceding embodiments, the natural substance is a plant of the plant family Simaroubaceae.

In any of the preceding embodiments, the natural substance is *Picrasma excelsa, Picrasma quassiodes, Quassia amara* or *Quassia africana*.

In any of the preceding embodiments, the natural substance includes bark of a plant of the plant family Simaroubaceae.

In any of the preceding embodiments, the natural substance includes heartwood of a plant of the plant family Simaroubaceae.

In any of the preceding embodiments, the natural substance includes bark and heartwood of a plant of the plant family Simaroubaceae.

In any of the preceding embodiments, the natural substance includes about 11% of the bark and about 89% of the heartwood.

In any of the preceding embodiments, the natural substance is in the form of wood chips.

In any of the preceding embodiments, the natural substance is in the form of wood meal.

In any of the preceding embodiments, the method further includes mixing the first spent natural substance with hot water to provide an aqueous phase of quassinoid.

In any of the preceding embodiments, the method further includes
(i) evaporating the second organic solvent from the second organic phase to yield a quassinoid residue; and
(ii) subjecting the residue in (i) to crystallization to yield crystalline quassinoid.

In any of the preceding embodiments, the method further includes mixing the second spent natural substance with hot water to provide an aqueous phase of quassinoid.

In any of the preceding embodiments, the first or second organic solvent is Generally Recognized As Safe (GRAS) by the U.S. Food and Drug Administration.

In any of the preceding embodiments, the first or second organic solvent is ethyl acetate.

In any of the preceding embodiments, the first or second organic solvent is selected from the group consisting of ether, methyl tert-butyl ether, ethyl-isopropyl ether, and higher ketones such as di-isopropyl ketone, dichloromethane, chloroform, carbon tetrachloride, other chlorinated solvents, and hydrocarbons such as benzene and toluene.

In any of the preceding embodiments, step b) or e) is conducted for less than or about 60 hours.

In any of the preceding embodiments, step b) or e) is conducted for less than or about 50 hours.

In any of the preceding embodiments, step b) or e) is conducted for less than or about 40 hours.

In any of the preceding embodiments, step b) or e) is conducted for less than or about 30 hours.

In any of the preceding embodiments, step b) or e) is conducted for less than or about 25 hours.

In any of the preceding embodiments, step b) or e) is conducted for less than or about 20 hours.

In any of the preceding embodiments, steps b) and e) are conducted for about 25 hours each.

In any of the preceding embodiments, step b) or e) is conducted for a time in a range of about 20-60 hours, about 25-50 hours, or about 30-40 hours.

In any of the preceding embodiments, step (b) further comprises stirring the first mixture.

In any of the preceding embodiments, step (e) further comprises stirring the second mixture.

In another aspect, a method of processing quassinoid from natural substance containing the quassinoid is provided, including:
(a) providing a first mixture comprising the natural substance comprising quassinoid and water, wherein the first mixture is free of organic solvent;
(b) extracting the quassinoid at room temperature to provide a first aqueous phase containing quassinoid; and
(c) extracting the quassinoid from the first aqueous phase with a first water-immiscible organic solvent to yield a first organic phase containing the quassinoid, wherein the natural substance comprises bark of a plant of the plant family Simaroubaceae.

In any of the preceding embodiments, the natural substance comprises bark and heartwood of a plant of the plant family Simaroubaceae.

In any of the preceding embodiments, the natural substance comprises bark and heartwood of a plant of the plant family Simaroubaceae in their naturally occurring ratio.

In any of the preceding embodiments, the natural substance comprises about 11% of the bark and about 89% of the heartwood.

In any of the preceding embodiments, step b) comprises applying ultrasonic energy directly to the first mixture to provide a first aqueous phase of the quassinoid and a first spent natural substance containing less quassinoid than the natural substance.

In yet another aspect, a method of processing quassinoid from a natural substance containing quassinoid, by indirect sonication is described, comprising:

(a) providing an original mixture comprising the natural substance containing quassinoid and an organic solvent mixture in a first container placed in a second container containing water, wherein the organic solvent mixture comprises one or more polar organic solvent and one or more non-polar organic solvent;

b) applying ultrasonic energy to the second container to result in a substantially quantitative extraction of the quassinoid from the natural substance into the organic solvent mixture; and (c) removing the spent natural substance from the extraction mixture to yield an organic phase containing the quassinoid, wherein the natural substance is a plant of the plant family Simaroubaceae or a portion thereof.

In any of the preceding embodiments, the method does not include a step of organic phase/aqueous phase partition.

In any of the preceding embodiments, the method does not include a step of organic phase/organic phase partition.

In any of the preceding embodiments, the method does not include a step of column chromatography.

In any of the preceding embodiments, the organic solvent mixture comprises two or more solvents selected from a group consisting of an ester, a hydrocarbon, an ether, and an alcohol comprising one to four carbons.

In any of the preceding embodiments, the ester is selected from the group consisting of methyl formate, methyl acetate, methyl propanoate, methyl butanoate, ethyl formate, ethyl acetate, ethyl propanoate, ethyl butanoate, propyl formate, propyl acetate, propyl propanoate, propyl butanoate, butyl formate, butyl acetate, butyl propanoate, butyl butanoate, and isomers thereof.

In any of the preceding embodiments, the hydrocarbon is selected from the group consisting of pentane, hexane, heptane, octane, and isomers thereof.

In any of the preceding embodiments, the alcohol is selected from the group consisting of methanol, ethanol, propanol, butanol, and isomers thereof.

In any of the preceding embodiments, the organic solvent is a mixture comprising at least two solvents selected form the group consisting of an ester, a hydrocarbon, and an alcohol comprising one to four carbons.

In any of the preceding embodiments, the organic solvent is a mixture of ethyl acetate, hexane, and ethanol.

In any of the preceding embodiments, ethyl acetate, hexane, and ethanol are in a 1:1:1, 1:2:1, 1:1:2, 2:1:1, 2:2:1, or 1:2:2 ratio by volume.

In any of the preceding embodiments, the organic solvent mixture is a mixture of ethanol and hexane.

In any of the preceding embodiments, ethanol and hexane are in a ratio by volume from about 1:2 to about 2:1.

In any of the preceding embodiments, the method further includes: (d) evaporating the organic solvent from the organic phase to yield a quassinoid residue; and (e) subjecting the residue in (d) to recrystallization to yield crystalline quassinoid.

In any of the preceding embodiments, the method further includes: (d) recrystallizing quassinoid from the organic phase to yield crystalline quassinoid.

In any of the preceding embodiments, the method further includes: the quassinoid comprises quassin and/or neoquassin.

In any of the preceding embodiments, the method further includes: the natural substance is a plant of the plant family Simaroubaceae.

In any of the preceding embodiments, the method further includes: the natural substance is *Picrasma excelsea, Picrasma quassiodes, Quassia amara* or *Quassia africana*.

In any of the preceding embodiments, the method further includes: the polar organic solvent and non-polar organic solvent are Generally Recognized As Safe (GRAS) by the U.S. Food and Drug Administration.

BRIEF DESCRIPTION OF THE DRAWINGS

A more complete appreciation of the present invention and many of its advantages will be understood by reference to the following detailed description when considered in connection with the following drawings, which are presented for the purpose of illustration only and are not intended to be limiting, and in which.

DETAILED DESCRIPTION

Figure 1B:
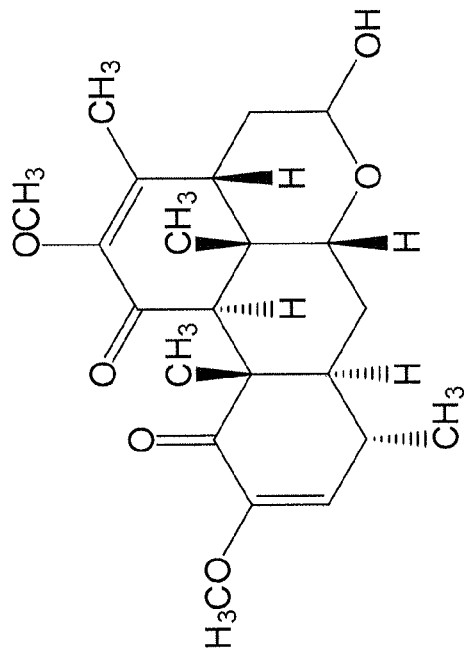
FIGS. 1A-1B illustrates the chemical structures of quassin (FIG. 1A) and neoquassin (FIG. 1B)
Figure 1A:
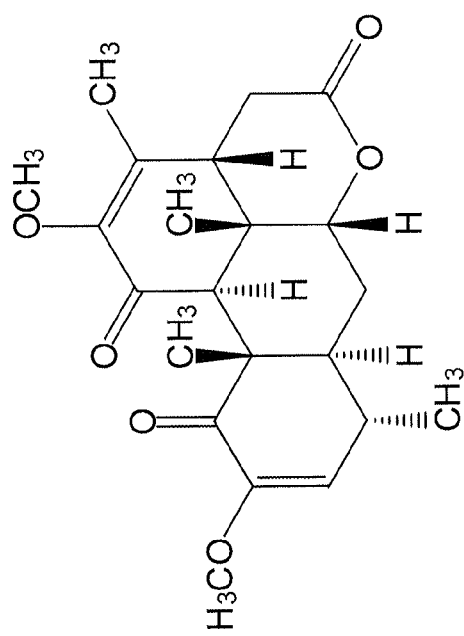

Methods of highly efficient extraction method for processing quassinoids are disclosed. In a first embodiment, the method comprises sonicating a mixture comprising non-organic solvent, i.e., water, and a natural substance containing quassinoids to provide an aqueous phase of the quassinoids. The method further comprises extracting quassinoids from the aqueous phase with a water-immiscible organic solvent. Notably, the process described in the first embodiments does not require the use of organic solvent in the initial extraction from natural substances. Additionally, the process described herein requires fewer number of steps and organic solvents, thus resulting in a highly efficient extraction method. In a second embodiment, the method comprises extracting quassinoid with water from the bark of a plant of the plant family Simaroubaceae. In a third embodiment, the method comprises extracting quassinoid by indirect sonication using a mixture of polar and non-polar organic solvents.

As is widely recognized in the field, extraction of organic natural product will be more efficient when an organic solvent is employed. (See, e.g., Celeghini et al., 2001, Extraction and Quantative HPLC Analysis of Coumarin in Hydroalcoholic Extracts of Mikania glomerata Spreng ("guaco") Leaves, J. Braz. Chem. Soc., Vol. 12, No. 6, 706-709). Celeghini et. al. teaches that the extraction by sonication in the 50% aqueous ethanol gives the best results compared with the extraction using boiling distilled water or supercritical carbon dioxide.

Applicants have surprisingly discovered that the extraction of quassinoids can be efficiently conducted using sonication with only water, e.g., without organic solvent. The extraction method disclosed herein results in a more efficient protocol of processing quassinoids including fewer steps and fewer number of organic solvents, with virtually the same yield. Because no organic solvents are used in the initial extraction step, the resulting aqueous phase from the initial extraction is substantially free of any non-polar impurities. Thus, a washing step to remove the non-polar impurities, e.g., a hexane washing step, can be omitted. Normally, salt such as sodium chloride is used to saturate the aqueous layer and facilitate the extraction of the organic material by an organic solvent, thus improving the extraction yield. Surprisingly, the step of saturating the aqueous phase with sodium chloride can be omitted as well without any loss of yield. Without being bound to any particular theory, it is believed that using organic solvent, e.g., ethanol, for extraction results in trace amounts of residual organic solvent remaining in aqueous phase. These residual solvents often lead to emulsification, so that the separation of the aqueous and organic phases is not sharp. Therefore, sodium chloride is usually added to increase the polarity of the aqueous phase and facilitate the separation of the two phases. The extraction method as disclosed herein involves no organic solvents in the initial extraction step, thus the addition of sodium chloride is no longer necessary. Additionally, since no organic solvent is used for the initial extraction, the evaporation step of the organic solvent can be omitted as well, resulting in a highly efficient processing method.

The method of processing quassinoids according to the first embodiment is described with reference to FIG. 2. In Step 201, natural substance containing quassinoids is subjected to sonication using non-organic media, e.g., water, as solvent. Non-limiting examples of quassinoids include quassin and neoquassin. Quassinoids are degraded triterpenoids, and are members of a large class of naturally occurring compounds derived from mevalonic acid. Natural substance includes any plants or other naturally-occurring substance that contains quassinoids. Non-limiting examples of natural substances that are high in quassinoid content include plants of the plant family Simaroubaceae such as Picrasma excelsa, (Jamaican Quassia); *Quassia amara*, (Surinam Quassia), *Picrasma quassioides*, and *Quassia Africana*. In some embodiments, the natural substance is a plant of the plant family Simaroubaceae or a portion thereof, e.g., bark or heartwood of the plant. In some embodiments, the wood chips of the naturally-occurring plants containing quassinoids are used for extraction. In some embodiments, commercial wood chips can be used. It is observed that after sonicating the commercial wood chips in the extraction, most of the wood chips tasted bland with a slight taste of bitterness, indicating that the process results in an almost complete extraction of the quassinoids. In other embodiments, the wood chips are chopped or broken into smaller pieces to reduce the wood particle size, prior to sonication. The reduction in wood chip sizes results in a more complete extraction of the chips. In some embodiments, the wood chips are chopped or broken into small slivers or pieces, approximately 25×3×2 mm. In other embodiments, the wood chips are chipped finer to a wood meal, e.g., of particle size <0.15 mm. In some embodiments, the small wood slivers or pieces or meal is dried before the sonication. In some specific embodiments, the wood chips, wood slivers, or wood meal are dried at approximately 70° C. for 2 days before sonication.

In some embodiments, an ultrasonic water bath is used. In some embodiments, the sonication extraction is conducted for less than or about 60 hours, less than or about 50 hours, less than or about 40 hours, less than or about 30 hours, less than or about 25 hours, or less than or about 20 hours. In some embodiments, the sonication extraction is conducted for about 50 hours, about 30 hours, about 25 hours, or about 20 hours. In some embodiments, the sonication extraction is conducted for a time in a range of about 20-60 hours, about 25-50 hours, or about 30-40 hours. In some embodiments, deionized water is used for extraction. In some other embodiments, more than one batch of water are used to avoid saturation of quassinoids in the aqueous medium. Replacing the aqueous extraction medium with a fresh batch of water during the extraction can improve the yield of the extraction. In some embodiments, after the initial extraction process, e.g., 20 h or 25 h after the start of the sonication, a first aqueous phase containing quassinoids is obtained, alone with a first spent natural substance, e.g., spent wood chips, containing substantially less quassinoid than the starting natural substance. In some embodiments, the first aqueous phase is removed and a fresh batch of water is added to the first spent natural substance. A second sonication is then conducted to result in a second aqueous phase containing quassinoids and a second spent natural substance. In some embodiments, the second sonication is conducted for about 20-25 h. Additional extraction steps, either using ultrasonic extraction or conventional solvent extraction, can be used.

In some embodiments, the extraction is carried out at room temperature. In other embodiments, the extraction is carried out at a temperature less than or about 40° C. In other embodiments, the extraction is carried out at temperature less than or about 50° C. In other embodiments, the extraction is carried out at temperature less than or about 60° C. In other embodiments, the extraction is carried out at a temperature in the range of about 25 to about 60° C. In other embodiments, the extraction is carried out at a temperature in the range of about 30 to about 55° C. In other embodiments, the extraction is carried out at a temperature in the range of about 35 to about 50° C. In other embodiments, the extraction is carried out at a temperature in the range of about 40 to about 50° C. The extractions of quassinoids at other temperatures are contemplated.

In some embodiments, the extraction mixture is stirred during the extraction. In some embodiments, the extraction mixture is stirred with a mechanical stirrer. Other stirring mechanisms and methods known in the art are also contemplated. The extraction mixture can be stirred continuously or intermittently.

In some embodiments, the method further comprises mixing the first or second spent natural substance with hot water to extract any residual quassinoids to provide an aqueous phase of quassinoids.

Figure 2:
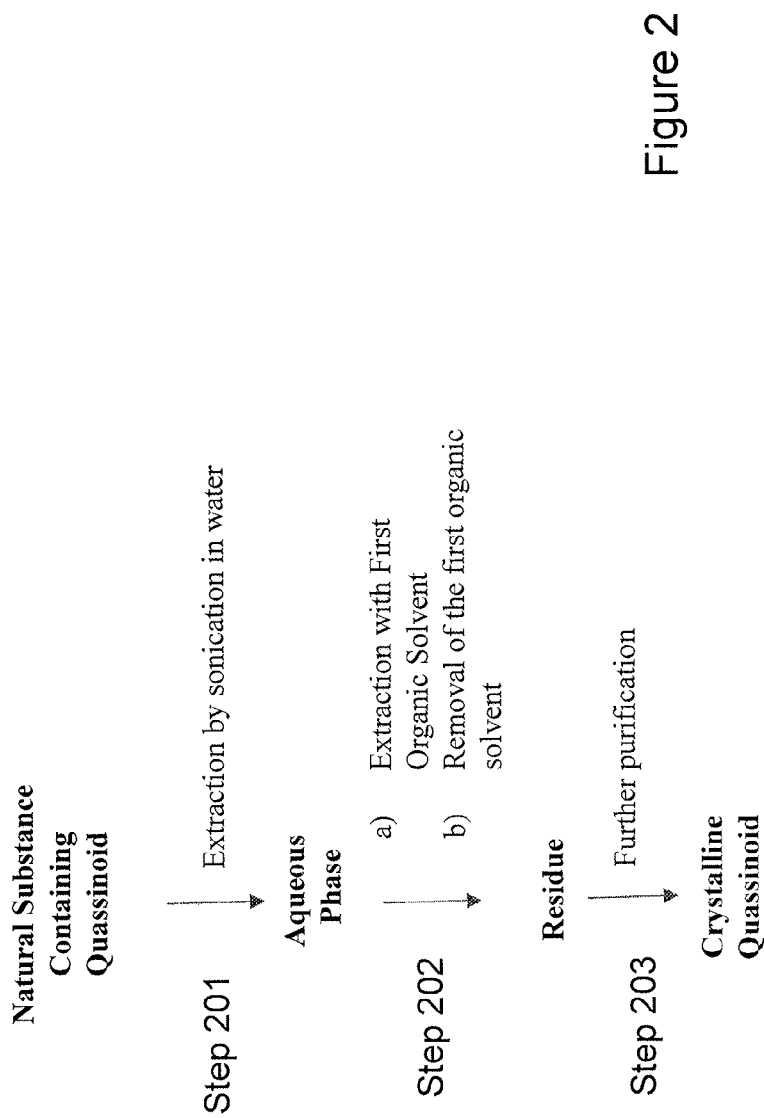
FIG. 2 is a schematic illustration of the extraction method of quassinoids according to one or more embodiments disclosed herein.

As shown by Step 202 a) of FIG. 2, after the aqueous phase containing quassinoids is obtained, the aqueous phase is subjected to extraction using a water-immiscible solvent, e.g., a first organic solvent, to provide an organic phase containing the quassinoids. In some embodiments, more than one aqueous phase are obtained, combined, and extracted with the water-immiscible solvent. In other embodiments, the aqueous phases are extracted separately by organic solvent and resulting organic phases are then combined. In some embodiments, ethyl acetate is used as the organic solvent. Other solvents known in the art are contemplated, including but are not limited to ether, methyl tert-butyl ether, ethyl-isopropyl ether, higher ketones such as di-isopropyl ketone, dichloromethane, chloroform, carbon tetrachloride, other chlorinated solvents, and hydrocarbons such as benzene and toluene. In some embodiments, the organic solvent, e.g., the first organic solvent, used for extraction is Generally Recognized As Safe (GRAS) by the U.S. Food and Drug Administration.

As shown by Step 202 b) of FIG. 2, the organic solvent is then removed from the extracted organic phase to afford a residue, e.g., a gum, containing quassinoids. In some embodiments, the organic solvent is removed by using a rotary-evaporator or other low pressure evaporating techniques. In other embodiments, the organic solvent is removed by distillation, freeze drying, and solvent evaporation aided with an inert gas including but not limited to nitrogen. Other methods for removing organic solvents known in the art are contemplated. A thin layer chromatogram of the residue can be used to identify the quassin or neoquassin in the residue.

In one embodiment, sonication of Bitterwood wood chip for 50 hours resulted in at least 98% of the quassin and neoquassin being extracted from the chips. Reducing the size of the wood chip increased extraction yield even further. Wood chip of average size of 25×3×2 mm resulted in a virtual complete extraction (e.g., >99%) of the quassinoids. Other suitable wood chip sizes are contemplated.

As shown by Step 203 of FIG. 2, the residue is then subjected to further purification. In some embodiments, the residue is further purified by re-crystallization. In some embodiments, crystalline seeds of quassinoids are used for seeding the crystals. The identity of the quassin/neoquassin can also be confirmed by thin layer chromatography and U.V. spectra comparisons with authentic quassinoids, e.g., quassin/neoquassin.

In other embodiments, column chromatography can be used to purify the quassinoids. In other embodiments, a combination of re-crystallization and column chromatography can be used. A detailed description of the re-crystallization and column chromatography methods is disclosed in U.S. Pat. No. 7,404,972, which is incorporated in its entirety by reference.

The method described herein can be used for the extraction of quassinoids from other simaroubaceous species or plant species containing quassinoids as well. Furthermore, the method described herein can be used for the extraction of other natural products contained in natural substances, wherein the natural product is at least sparingly soluble in water.

A second embodiment of extracting quassinoids using a natural substance is described. In some embodiments, the natural substance includes a tree which is a plant of the plant family Simaroubaceae. In some embodiments, the tree includes *Picrasma excelsea, Picrasma quassiodes, Quassia amara* or *Quassia Africana*. The natural substance includes bark of the tree, heartwood of the tree, and a combination thereof. Any bark of a tree which contains quassinoids can be used as the natural substance for extracting quassinoids using methods disclosed herein. In some embodiments, the natural substance for extraction used contains a mixture of tree bark and wood chip in the naturally occurring ratio. The method comprises: (a) providing a first mixture of the natural substance with water, wherein the first mixture is free of organic solvent; (b) extracting the quassinoid at room temperature to provide a first aqueous phase containing quassinoid; and (c) extracting the quassinoid from the first aqueous phase with a first water-immiscible organic solvent to yield a first organic phase containing the quassinoid.

As noted above, the bark of a tree usually is not considered as a viable source for the extraction of quassinoids, due to the fact that the extracts from barks contain more impurities and exhibit dark colors. It has been surprisingly found that using methods disclosed herein, a bark of a tree containing quassinoids can be used as a source to extract quassinoids efficiently, affording quassinoids with high purities. Without being bound to any particular theory, it is believed that the extraction method disclosed herein utilizes non-organic solvent as the extracting solvent, thus efficiently reducing the amount of non-polar impurities in the extract. The non-polar impurities are believed to be the primary source of the impurity and discoloring observed during conventional process. Additionally, the extraction of the quassinoid is conducted at room temperature, thereby further reducing the amount of impurities dissolved during extraction. In other embodiments, the extraction is carried out at a temperature less than or about 40° C. In other embodiments, the extraction is carried out at temperature less than or about 50° C. In other embodiments, the extraction is carried out at temperature less than or about 60° C. In other embodiments, the extraction is carried out at a temperature in the range of about 25 to about 60° C. In other embodiments, the extraction is carried out at a temperature in the range of about 30 to about 55° C. In other embodiments, the extraction is carried out at a temperature in the range of about 35 to about 50° C. In other embodiments, the extraction is carried out at a temperature in the range of about 40 to about 50° C. The extractions of quassinoids at other temperatures are contemplated.

In some embodiments, the bark of Bitterwood, *Picrasma excels*, is used as the natural substance for extraction. A crude extraction of the bark tastes bitter and also shows U.V. absorption at 255 nm, indicating that it contains quassinoids. In some embodiments, the concentration of quassinoids is shown to be higher in the bark than in the heartwood. Natural resources include tree bark, such as the tree barks of *Quassia amara, Picrasma quassioides*, and *Quassia africana*.

Figure 3:
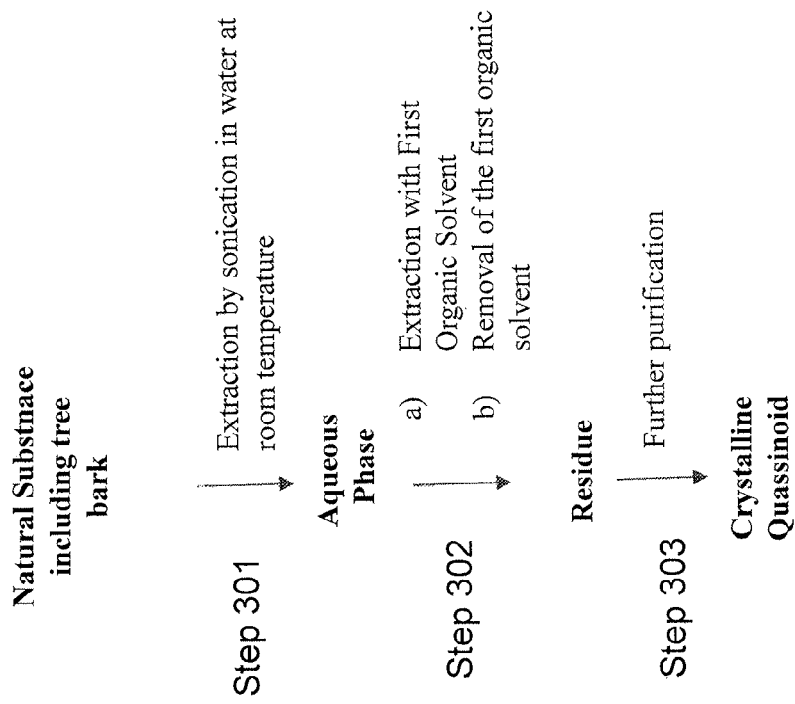
FIG. 3 is a schematic illustration of the extraction method of quassinoids from natural substances including bark according to one or more embodiments disclosed herein.

In some embodiments, quassinoid are extracted from bark of Bitterwood, Picrasma excelsa, using the method described in FIG. 3. As shown in FIG. 3, a natural substance including tree bark is subjected to sonication extraction using water as solvent at room temperature. Without being bound to any particular theory, it is believed that sonication improves the efficiency of the extraction and the use of low temperature and non-organic extraction solvent efficiently reduces the non-polar impurities. In some embodiments, the natural substance is a bark of a tree of the plant family Simaroubaceae. In some embodiments, the tree is *Picrasma excelsea, Picrasma quassiodes, Quassia amara* or *Quassia Africana*. In some embodiments, natural substance is a mixture of the bark and heartwood of the plant. In some embodiments, the mixture comprises about 11 wt % of the bark and about 89 wt % heartwood of the plant, which corresponds to the natural composition normally presented in the tree.

In Step 301, natural substance, e.g., tree bark, containing quassinoids is subjected to sonication using water as solvent. As shown by Step 302 a) of FIG. 3, after the aqueous phase containing quassinoids is obtained, the aqueous phase is subjected to extraction using a water-immiscible solvent, e.g., a first organic solvent, to provide an organic phase containing the quassinoids. In some embodiments, more than one aqueous phase are obtained, combined, and extracted with the water-immiscible solvent. In other embodiments, the aqueous phases are extracted separately by organic solvent and the resulting organic phases are then combined. In some embodiments, ethyl acetate is used as the organic solvent. Other solvents known in the art are contemplated, including but are not limited to ether, methyl tert-butyl ether, ethyl-isopropyl ether, higher ketones such as di-isopropyl ketone, dichloromethane, chloroform, carbon tetrachloride, other chlorinated solvents, and hydrocarbons such as benzene and toluene. In some embodiments, the organic solvent, e.g., the first organic solvent, used for extraction is Generally Recognized As Safe (GRAS) by the U.S. Food and Drug Administration.

As shown by Step 302 b) of FIG. 3, the first organic solvent is then removed to afford a residue, e.g., a gum, containing quassinoids. In some embodiments, the organic solvent is removed by using a rotary-evaporator or other low pressure evaporating techniques. Other methods for removing organic solvents known in the art are contemplated. In other embodiments, the organic solvent is removed by distillation, freeze drying, and solvent evaporation aided with an inert gas including but is not limited to nitrogen. Thin layer chromatography of the residue can be used to identify the quassin or neoquassin in the residue.

As shown by Step 303 of FIG. 3, the residue is then subjected to further purification. In some embodiments, the residue is further purified by re-crystallization or column chromatography. In some embodiments, crystalline seeds of quassinoids are used for seeding the crystals. The identity of the quassin/neoquassin can also be confirmed by thin layer chromatography and U.V. spectra comparisons with authentic quassinoids, e.g., quassin/neoquassin.

In some embodiments, the use of natural substances including bark containing quassinoids results in quantitative extraction of the quassinoids. In some embodiments, the extraction results in a commercially suitable yellow or pale yellow extract. In some embodiments, the color of the extracted gum from sources including bark is quite clear and was of a similar appearance to the gum obtained from the extraction of the heartwood chips only. In some embodiments, a decolorizing agent is used to remove the color of the extracted quassinoid. Non-limiting examples of decolorizing agents include charcoal. The gum can be induced to crystallize with mixed crystals of quassin/neoquassin. The crystallization methods include, but are not limited to, seeding the extraction solution with quassinoid crystals. The extraction solvent can be concentrated before crystallization.

Accordingly, a suitable method to extract the quassinoids from the bark of the tree is disclosed. The bark is normally discarded as a waste material, although it is demonstrated that the bark contains a greater concentration of quassinoids than the heartwood chips. Without wishing to be bound to any particular theory, it is believed that the extraction method disclosed in prior art utilizes organic solvent to extract quassinoids from the bark, which results in excess amount of impurities being extracted into the quassinoid product mixture. Due to the presence of these excess amount of impurities, purification of the quassinoid via method such as re-crystallization is very difficult. In sharp contrast, the method disclosed herein does not require organic solvent during the initial extraction step of the natural substance containing quassinoid. As a result, the amount of impurities in the extraction mixture is greatly reduced and the quassinoids are purified by re-crystallization without much difficulties. The ability to use the bark of the tree will allow for a greater conservation of the tree and would allow for the harvesting of fewer trees for the trade. In some embodiments, the disclosed methods involve the use of water as the first extracting solvent, followed by extraction using organic solvent, e.g., ethyl acetate, which is recyclable, thus resulting in a relatively low cost methodology of extraction of the quassinoids.

A third embodiment provides a highly efficient extraction method for processing quassinoids using indirect sonication. The method comprises (a) providing an original mixture comprising the natural substance and an organic solvent mixture in a first container placed in a second container containing water, wherein the organic solvent mixture comprises one or more polar organic solvents and one or more non-polar organic solvents; b) applying ultrasonic energy to the second container to result in a substantially quantitative extraction of the quassinoid from the natural substance into the organic solvent mixture; and (c) remove the spent natural substance from the extraction mixture to yield an organic phase containing the quassinoid. Optionally, the organic solvent mixture may be further mixture with water to optimize the property of the solvent mixture in the first container used for extraction. In some embodiments, only non-aqueous organic mixture is used in the first container for indirect sonication extraction.

In direct sonication, the use of only organic solvent(s) is generally considered to be dangerous as it may result in fire or explosion when the organic solvent issonicated. See, Operator's Manual, CPN-214-151, Bransonic Ultrasonic Cleaners, Branson Ultrasonics B. V., Netherlands. Thus, generally, water or at least partially aqueous medium is used for direct sonication. In contrast, indirect sonication allows the use of only organic solvent for the extraction without the danger of fire or explosion. For instance, in an indirect sonication, the substance to be extracted can be mixed with one or more organic solvents in a first (smaller) container. The smaller container is then placed in a second (bigger) container filled with aqueous media. Ultrasonic energy is then applied to water in the bigger container and then transferred to the smaller container and in turn the mixture inside the smaller container. When the smaller container contains organic solvent, the organic solvent and the substance to be extracted are indirectly sonicated and thus the danger of explosion or fire by the organic solvent is greatly reduced.

In one or more embodiments, quassinoids are extracted from natural substances by using indirect sonication. In these embodiments, one or more suitable organic solvents are mixed with a natural substance containing quassinoids for quassinoid extraction. In some embodiments, a mixture of organic solvents are selected based on the solvent(s)'s polarities, dissolving capabilities, and other relevant properties so that after the extraction process, the quassinoid in the natural substance is substantially quantitatively extracted into the organic solvent while the amount of polar and non-polar impurities extracted is minimized. In some specific embodiments, a mixture of one or more polar organic solvents and one or more non-polar organic solvents is used in indirect sonication. The use of a mixture of polar and non-polar organic solvents results in a solvent system which maximizes the quassinoids extracted and at the same time, minimizes the impurities extracted.

In the indirect sonication, the natural substance, e.g., heartwood chip, to be extracted is not placed directly in the ultrasonic bath with the extracting solvent but instead is contained in a vessel with flammable organic solvents, where the ultrasonic waves are allowed instead to pass through the walls of the vessel into the extracting mixture and in this manner to extract the wood chips.

Figure 5:
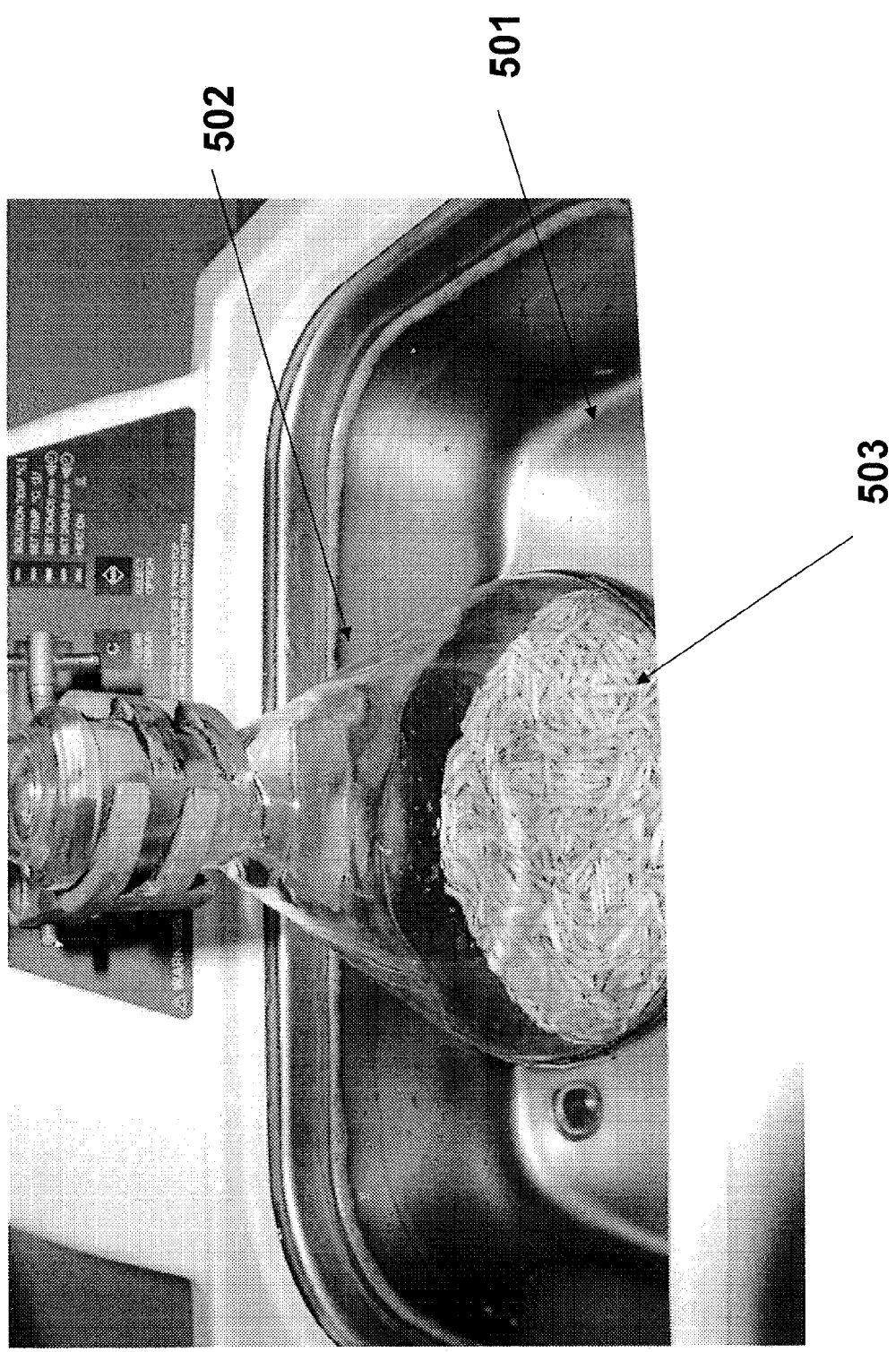
FIG. 5 shows an apparatus set up for quassinoid extraction using indirect sonication accordingly to one or more embodiments disclosed herein.

An apparatus set up for quassinoid extraction using indirect sonication accordingly to one or more embodiments is shown in FIG. 5. Natural substance 503 containing quassinoids, e.g., heartwood or bark of a plant of the plant family Simaroubaceae, is placed in a smaller container 502. One or more suitable organic solvents are then added into 502. Container 502 is then placed into a bigger container 501 containing water, which is then subjected to sonication. The ultrasonic energy is applied to water in 501, and then indirectly to the mixture in container 502.

Figure 6:
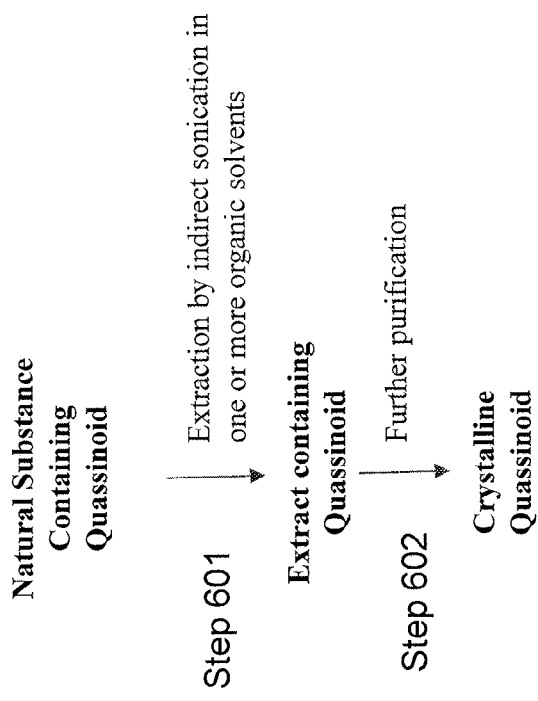
FIG. 6 is a schematic illustration of the extraction method of quassinoids from natural substances using indirect sonication according to one or more embodiments disclosed herein.

FIG. 6 is a schematic illustration of the extraction method of quassinoids from natural substances using indirect sonication according to one or more embodiments disclosed herein. In Step 601, natural substance, e.g., tree bark or heartwood containing quassinoids, is subjected to indirect sonication using one or more organic solvents. The resulting organic phase containing quassinoid is then subjected to further purification to yield crystalline quassinoid (Step 602).

If the extraction phase contains excess amount of polar impurities or nonpolar impurities, it will be difficult to purify the quassinoid by recrystallization as the impurities will interfere with the formation of crystalline quassinoid. The polar impurities need to be removed by methods known in the art, e.g., a partition between the organic phase containing the quassinoids and an aqueous phase. The non-polar impurities need to be removed by methods known in the art, e.g., a partition between the organic phase containing the quassinoids and an immiscible non-polar organic phase. Thus, it is desirable to reduce the amount of the impurities extracted from the natural substance and thus the extraction process can be simplified.

As used herein, the quassinoid in the natural substance is substantially quantitatively extracted into the organic solvent when more than about 90%, about 95%, or about 99% of the quassinoid in the natural substance is extracted into the organic solvent used. Generally speaking, quassinoids may also be purified by column chromatography. However, in large-scale purifications, column chromatography can be tedious and time-consuming. In comparison, recrystallization method works well on large-scale preparations and results in quassinoids with high purity. In some embodiments, the indirect sonication method minimizes the polar and non-polar impurities extracted into the organic phase so that quassinoids can be easily recrystallized. In some embodiments, the quassinoid-processing method utilizing indirect sonication does not include a step of organic phase/aqueous phase partition, a step of organic phase/organic phase partition, and/or a step of column chromatography.

In some embodiments, a mixture of two or more organic solvents is used to extract the quassinoids. Applicants have surprisingly discovered that by using a mixture of organic solvents, one may fine-tune the properties of the organic solvent mixture so that during the extraction, substantially all of the quassinoid in the natural substance is extracted into the mixture while the amount of impurities extracted into the mixture of organic solvents is minimized. By selecting two or more different organic solvents in the multi-solvent extraction process, one may fine-tune the solvents' properties such as dissolving capability, polarity, etc., so that the polar and non-polar impurities extracted into the organic phases are minimized, while maintaining a substantially quantitative extraction. For instance, when a mixture of a polar organic solvent and a non-polar organic solvent is used for extraction, the polar solvent, usually with greater quassinoid-dissolving ability, will help maximize the quassinoid extraction yield, and the non-polar organic solvent will help decrease the overall polarity of the solvent system to limit the amount of polar impurities extracted into the solvent system. Likewise, the presence of polar organic solvent also helps to limit the amount of non-polar impurities extracted to the solvent mixture. Without wishing to be bound by any particular theory, it is believed that the quassinoids to be extracted are relatively polar, and that non-polar impurities can render the crystallization of the quassinoids difficult or even impossible. By a careful choice of solvent mixtures, all of the quassinoids in the natural substance are extracted but yet the extraction of the non-polar substances is avoided. For instance, by using a solvent mixture of hexane:ethanol (50%:50%), it is possible to extract a highly pure mixture of quassin/neoquassin which readily crystallized in the evaporating flask upon evaporation. In another specific embodiment, a solvent mixture of 50% hexane, 25% ethyl acetate, and 25% ethanol is utilized for the quassinoid extraction. In some embodiments, the crude quassinoid extract comprises less than about 15%, about 10%, about 5%, about 1%, or about 0.5% of impurities. In some embodiments, the amount of impurities in the crude extract is minimized so that quassinoid can be crystallized directly from the crude mixture.

After the initial extraction of quassinoid, the extraction mixture may be filtered to remove the spent natural substance to result in an organic phase containing quassinoids. In some specific embodiments, the resulting organic phase is used directly for quassinoid recrystallization. A portion of the organic solvent is removed, and/or seeds of quassinoid crystals may be added to facilitate the recrystallization. In other specific embodiments, the solvent in the organic phase is removed to yield a residue, which is then subjected to recrystallization to yield crystalline quassinoid.

In some embodiments, the organic solvent system comprises two or more solvents selected from a group consisting of an ester, a hydrocarbon, an ether, and an alcohol comprising one to four carbons. Preferably, the organic solvent system comprises a mixture of one or more polar organic solvents, e.g., ether, ester, or alcohol, and one or more non-polar organic solvents, e.g., hydrocarbon. Non-limiting examples of esters include methyl formate, methyl acetate, methyl propanoate, methyl butanoate, ethyl formate, ethyl acetate, ethyl propanoate, ethyl butanoate, propyl formate, propyl acetate, propyl propanoate, propyl butanoate, butyl formate, butyl acetate, butyl propanoate, butyl butanoate, and isomers thereof. Non-limiting examples of hydrocarbons include pentane, hexane, heptane, octane, and isomers thereof. Non-limiting examples of alcohol include methanol, ethanol, propanol, butanol, and isomers thereof. In some embodiments, the organic solvent sued is Generally Recognized As Safe (GRAS) by the U.S. Food and Drug Administration.

The step b) in the indirect sonication method described above can be conducted for less than or about 60, 50, 40, 30, 25, or 20 hours. Specifically, the step c) can be conducted for a time in a range of about 20-60 hours, about 25-50 hours, or about 30-40 hours.

In some embodiments, the method further comprises (d) evaporating the organic solvent from the organic phase to yield a quassinoid residue; and (e) subjecting the residue in (d) to recrystallization to yield crystalline quassinoid. In some embodiments, the method further comprises (d) recrystallizing quassinoid from the organic phase to yield crystalline quassinoid.

In some embodiments, the solvent used for indirect sonication of quassinoids is a mixture comprising at least two solvents selected form the group consisting of an ester, a hydrocarbon, and an alcohol comprising one to four carbons. In some specific embodiments, the organic solvent is a mixture of an ester, a hydrocarbon, and an alcohol comprising one to four carbons. The volume ratios of ester:hydrocarbon:alcohol may be 1:1:1, 1:2:1, 1:1:2, 2:1:1, 2:2:1, or 1:2:2. In some embodiments, the organic solvent mixture includes about 10% to about 40% ester, 10% to about 50%, and about 40% to about 80% alcohol by volume. Other proper ratios are contemplated. In some specific embodiments, the organic solvent is a mixture of ethyl acetate, hexane, and ethanol. The ethyl acetate:hexane:ethanol volume ratio may be 1:1:2 or other proper ratios to ensure substantially quantitative quassinoid extraction while minimizing the amount of impurities extracted.

In other specific embodiments, the organic solvent used for indirect sonication is a mixture of ethyl acetate and hexane. The hexane:ethanol volume ratio may be 1:1 or other proper ratios to ensure substantially quantitative quassinoid extraction while minimizing the amount of impurities extracted. In some embodiments, the hexane/ethanol volume ratio is from about 1:10 to about 10:1, from about 1:1 to about 10:1, from about 1:1 to about 2:1, from about 1:10 to about 1:1, from about 1:10 to about 1:5, from about 1:8 to about 1:5, from about 1:6 to about 1:5, from about 10:1 to about 10:5, from about 8:1 to about 4:1, from about 5:1 to about 2:1, from about 2:1 to about 1:2, or from about 2:1 to about 1:1. In some embodiments, the hexane/ethanol volume ratio is about 10:1, 9:1, 8:1, 7:1, 6:1, 5:1, 4:1, 3:1, 2:1, 1:1, 1:2, 1:3, 1:4, 1:5, 1:6. 1:7, 1:8, 1:9, or 1:10. In some embodiments, a portion of the hexane/ethanol mixture is removed and the quassinoid crystallizes out of the solution. In some embodiments, seeds of quassinoid crystals is added into the hexane/ethanol phase and the quassinoid crystallizes out of the solution.

Thus, in some embodiments, the indirect sonication of natural substance, e.g., Bitterwood chips, leads to a facile extraction of the wood chips where it is possible to extract fairly pure crystals of quassin/neoquassin efficiently with a solvent mixture described herein. In effect, it is therefore possible to go from wood chips to fairly pure crystals in one step by indirect sonication and with merely the evaporation of the solvent mixture required afterwards.

Any natural substance containing quassinoids maybe used in the indirect sonication. The natural substance can be a plant of the plant family Simaroubaceae. In some embodiments, the natural substance used is *Picrasma excelsea, Picrasma quassiodes, Quassia amara* or *Quassia Africana*. As described herein, any portion of the plant, e.g., bark or heartwood, can be used in indirect sonication.

Figure 7:
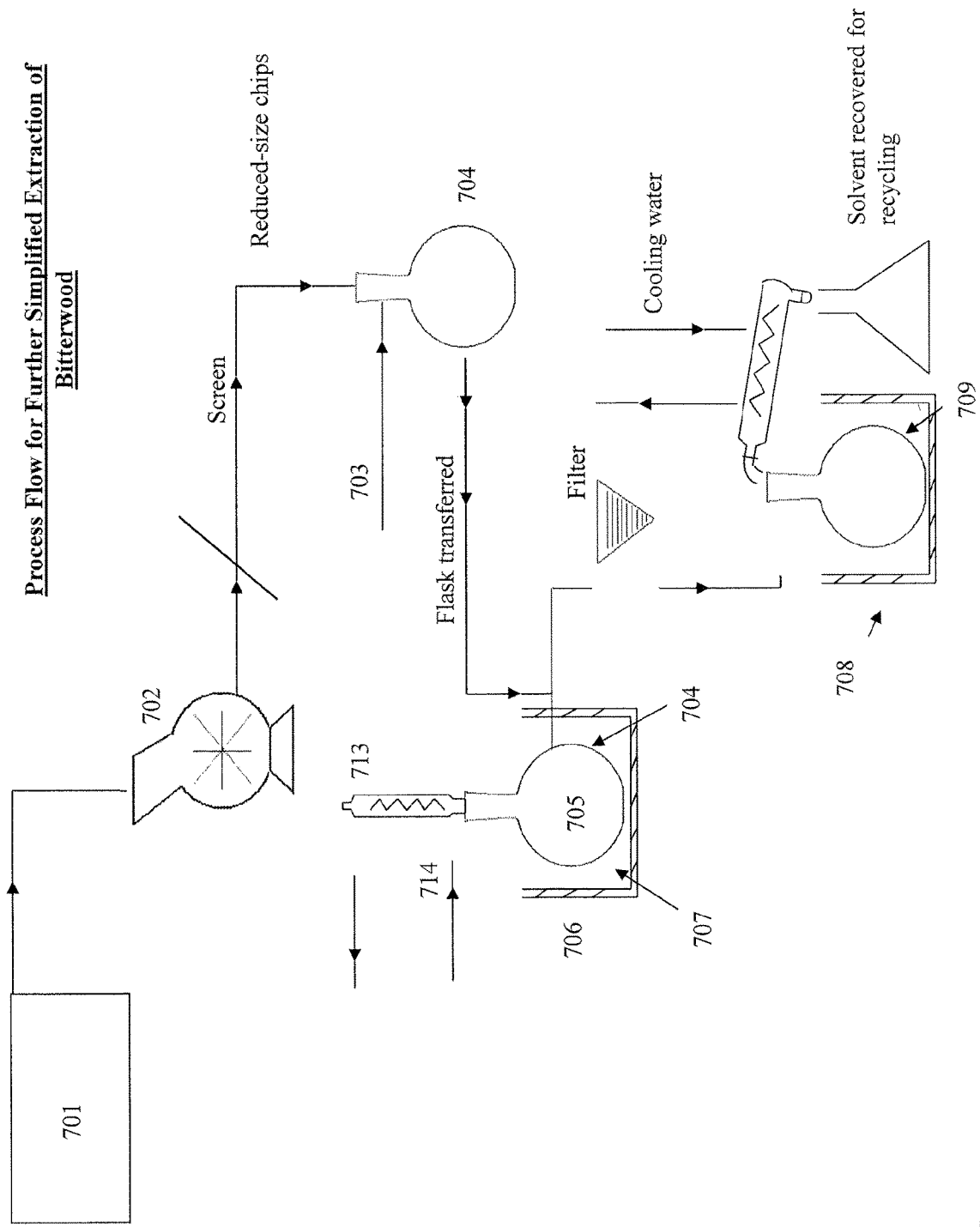
FIG. 7 is a flow chart illustration of the extraction process of quassinoids from natural substances using indirect sonication according to one or more embodiments disclosed herein.

FIG. 7 shows a flow chart illustration of the extraction process of quassinoids from natural substances using indirect sonication according to one or more embodiments disclosed herein. Natural substance containing quassinoids, e.g, heartwood or bark chips of a plant of the plant family Simaroubaceae, from commercial chips storage 701 is transferred into a chipper 702 to reduce the chips to proper size. After initial screening, reduced-size chips are placed in a container 704, e.g., a flask. Organic solvent(s) 703 are then added into 704. The flask 704 is then transferred into a sonicator 706 containing aqueous media 707. As described herein, the organic solvent(s) are selected so that the overall property of the organic solvent(s) is such that the quassinoid in the natural substance is substantially quantitatively extracted into the organic solvent while the amount of polar and non-polar impurities extracted is minimized. When the organic solvent used is a mixture of several organic solvents, the evaporation of one of the organic solvent in the mixture may affect the overall dissolving capability or polarity of the solvent mixture. As a result, the amount of impurities extracted may increase and/or the amount of quassinoids extracted may decrease. Thus, the flask 704 has a reflux condenser 713 attached to it, which has cooling water 714 running through the condenser 713 to prevent or minimize any evaporation of the organic solvent.

As further shown in FIG. 7, after indirect sonication, the mixture 705 in flask 704 is filtered to remove the spent heartwood or bark chips and the resulting organic phase containing quassinoid is placed in flask 709. Flask 709 is then heated using a hot water or steam bath or a rotavapor, ect., 708 to remove all or a portion of the organic solvent (which is recovered for recycling) so that quassinoid is crystallized. Quassinoid crystal seed may optionally be added into flask 709 to facilitate the crystal formation.

EXAMPLES

Preparation and Drying of Wood Chips

The heartwood of Bitterwood trees are commercially chipped to chips of approximate size of 50×30×5 mm. for the initial extraction. Samples of these chips were then further reduced in size to chips of approximately 25×3×2 mm. or to a wood meal approx size, 0.15 mm, for the subsequent extractions. All the chips were dried at approximately 70° C. for approximately 2 days.

Initial Extraction of Wood Chips by Sonication in Water

Commercial dried Bitterwood chips (150 g) were placed in a Branson 3510 Ultrasonic Bath, to which was added deionized water (5 L) and the mixture subjected to ultrasonic sound waves. The sonication was continued for approximately 28 hrs after which time most of the bitterness of the wood chips was considerably reduced. The aqueous solution was removed and extracted with ethyl acetate (4×500 ml), and the ethyl acetate evaporated to leave a gum (0.8355 g, 71.36% of total gum extracted). The wood chips were then re-sonicated with water (5 L) for a further 7 hrs, the aqueous fraction again extracted with ethyl acetate (4×500 ml) to yield an additional gum (0.3354 g, 28.64% of total gum extracted). The two extracted gums were combined (1.171 g, 0.78% w/w). A thin layer chromatography of the gum showed that it was rich in quassin and neoquassin and upon seeding with the crystals of quassin and neoquassin, a solution of the gum in ethanol, readily crystallized into a mass of crude crystals. A U.V. spectrum of the gum showed the characteristic absorption peak for quassin at 255 nm. There was, however, still a residual bitterness in especially the thicker chips although the smaller ones were bland to the taste. Repeated extraction of the wood chips (with reduction of the size of the chips) was done until the wood chips tasted completely bland indicating that all of the quassinoids had been extracted.

Another sample of wood chips was chopped or broken into small slivers or pieces of a particle size of approximately <0.15 mm. 125 g of this wood meal was placed in the ultrasonic bath in water (5 L) and sonicated for 28 hrs. The aqueous fraction was then removed and extracted with ethyl acetate (4×500 ml.) and the ethyl acetate fraction evaporated to dryness to a yellow gum (0.5161 g, 77.74% of extracted gum). The wood meal was then re-sonicated in water (5 L) for a further 7 hrs and the water fraction removed and extracted with ethyl acetate (4×500 ml) and the ethyl acetate fraction evaporated to dryness to a yellow gum (0.1109 g, 16.70% of extracted gum). Most of the bitterness was removed from the wood meal but a very slight trace of bitterness was perceived. The wood meal was then infused in hot previously boiling water (2 L) for a further 4 hrs then the aqueous fraction extracted in the usual manner with ethyl acetate (4×150 ml.) to give a yellow gum (0.0369 g, 5.56% of extracted gum) after which the wood meal tasted completely bland, indicating that all the quassinoids had been extracted. A thin layer chromatography of the combined gum again showed that it was rich in quassin and neoquassin. Upon seeding with authentic crystals of quassin and neoquassin, the gum readily crystallized into a mass of crystals and a U.V. spectrum of the crystal showed the absorption peak characteristic of quassin at 255 nm.

Repeated Extraction of the Wood Chips, with Sonication for Longer Period of Time 100 g of wood chips of another wood sample of approximate size 25×3×2 mm. were sonicated in the usual manner in 5 L deionized water. The wood chips were sonicated for a total of 50 hrs, with a changing of the sonicating medium after 25 hrs. After 50 hrs, the wood chips were very bland to the taste indicating that all or virtually all of the quassin and neoquassin contained in them had been extracted, and the sonication ceased. Extraction of the water fractions by ethyl acetate in the manner described above yielded a gum after 25 hrs of sonication (0.7104 g, 82.98%), and a further gum (0.1295 g, 15.13%) after 50 hrs sonication. The wood chips after the sonication process was soaked in hot, previously boiling water for 4 hrs, and this final aqueous fraction was extracted with ethyl acetate in the usual manner to yield a gum (0.0162 g, 1.89%), showing that the extraction was 98% complete after 50 hrs sonication. A thin layer chromatogram of the gum showed that it was rich in quassin and neoquassin. Upon seeding with authentic crystals of quassin and neoquassin, an ethanol solution of the gum readily crystallized, and a U.V. spectrum of the gum gave the characteristic absorption peak for quassin of 255 nm.

Extraction of Quassinoids from Natural Substances Including Tree Bark by Sonication in Water The concentration of quassin in the chips from the heartwood was measured and compared with that contained in the bark, by measuring the U.V. absorption at 255 nm, which is characteristic of quassin.

The bark, which is usually discarded as a waste material, was found to contain more quassin than the heartwood chips. A comparison of the weights of the bark to that of the heartwood, revealed that approx. 11% of the weight of the wood is bark, and that at current exports of approx. 200,000-250,000 Kg of heartwood chips per annum, that approx. 25-30 tonnes? (tons) of bark are discarded annually.

Figure 4:
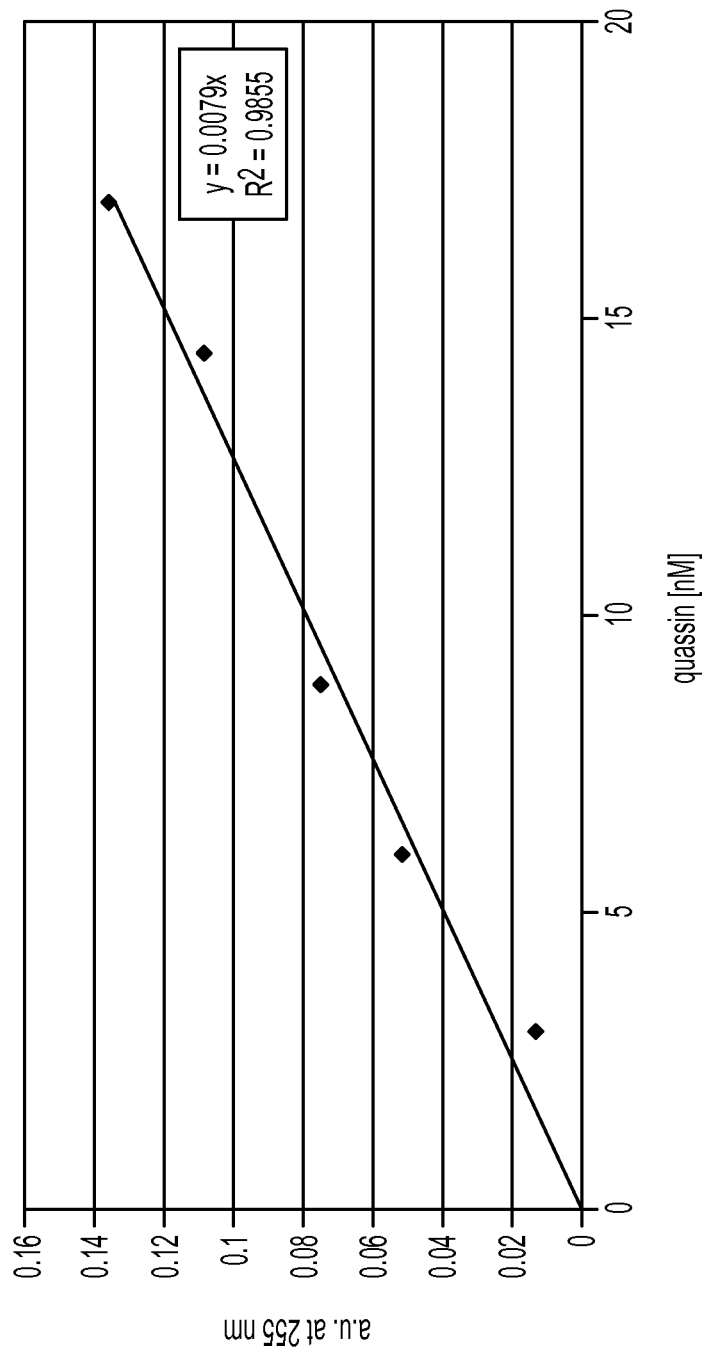
FIG. 4 shows the absorption of quassin at 255 nm in relation to the quassin's concentrations.

In order to compare the quantities of quassin/neoquassin that were extracted from the wood samples, a graph was generated by preparing standard solutions of quassin and plotting the absorption of quassin at 255 nm versus its concentration in moles (see FIG. 4). As shown in FIG. 4, the characteristics of the graph obtained were described by the values, y=0.0079x, and $R^2$=0.9855.

Using this method, the quassin concentrations of the heartwood chips, the bark, and the heartwood chips and bark in the normal concentration in the wood were determined as follows: 1.39%, 2.12%, and 1.49%, respectively.

Detailed Description of the Process

Samples of chips from the heartwood, the bark, and the heartwood chips mixed with bark chips in the amounts contained naturally in the tree were subjected to sonication in water as described herein. The method extracted the quassinoids quantitatively, and after the extraction process all the extracted wood chips were completely bland to the taste indicating the complete removal of the quassinoids that had been present in them. In the process 100 g of each wood sample, that is of heartwood chips, or bark chips, or mixed heartwood and bark chips were placed in an ultrasonic bath, and extracted in water. All the extractions were done in duplicate and an average of the two readings for each extraction was used in calculations. The aqueous solutions were then extracted with ethyl acetate, and the solvent removed to leave gums, the t.l.c.'s of which all indicated that quassin/neoquassin were the principal components.

Extraction of Heartwood Chips

Heartwood chips (100 g) were placed in the ultrasonic bath with deionized water (5.5 L). After 40 hrs sonication, the extraction was complete and the wood chips were completely bland to the taste. In order to improve the efficiency of the extraction it had been found desirable to change the extracting water at least once in the process to avoid saturation. For this purpose, after 15 hours sonication, the water used for extraction the initial water had been removed and fresh water used. After the 40 hrs of sonication, the extracting water was decanted and hot boiling water (3 L) was then used to strip any remaining quassinoids from the wood chips. The quassinoids in the water fractions were extracted with ethyl acetate and the solvent removed in vacuo to leave a gum (0.8686 g), the tlc of which showed that the principal components were quassin/neoquassin. U.V. analyses at 255 nm indicated the quassin concentration in the heartwood chips as 1.39% w/w. The gum could be induced to crystallize as a mass containing mixed crystals of quassin/neoquassin by seeding.

Extraction of the Bark Chips

Bark chips (100 g) were extracted as above. The time for sonication of the bark was longer than for the heartwood chips and was completed after 66 hrs of sonication, with a change of the water used for extracting after 46 hrs Extraction of the aqueous fractions with ethyl acetate resulted in a gum (1.0804 g), which was darker in color than that of the chips only. The tlc indicated that quassin/neoquassin were the main components in the gum, the quantitative U.V. analysis of which indicated that the quassin content of the bark was 2.12% w/w. The gum could be induced to crystallize by the addition of mixed crystals of quassin/neoquassin.

Extraction of Mixed Heartwood and Bark Chips in the Amounts Normally Found in the Wood Mixed heartwood and bark chips (100 g) in the ratio of 89% heartwood to 11% bark found to be the normal ratio in the wood, were extracted in the manner above by sonication in water. Extraction was complete after 40 hrs sonication, the extracting water having been changed after 25 hrs. After extraction of the water fractions with ethyl acetate and evaporation of solvent, a gum (0.8965 g) was obtained, the tlc of which indicated that quassin/neoquassin were the main components, and the quantative U.V. analyses of which indicated that the quassin content of the mixed chips was 1.49% w/w. The color of the extracted gum was quite clear and was of a similar appearance to the gum obtained from the extraction of the heartwood chips only. The gum could be induced to crystallize with mixed crystals of quassin/neoquassin.

Therefore, extraction of a mixture of bark and heartwood as it is normally present in the wood, i.e. 11% bark and 89% heartwood, results in quantitative yield of quassinoids with a fairly clear extract.

Detailed Description of the Extraction Process Using Indirect Sonication

It was found that the method was quite efficient and that the extraction times were comparable to the extractions with direct sonication of the wood chips using water in the extraction process as described above. An investigation into the scope of the method was investigated by the use of a number of solvents and solvent mixtures.

In the first extractions using this latest process, it was found that ethanol extracted all the quasinoids from the wood chips in a comparable time to that achieved in the direct sonications. Ethanol was found, however, to have extracted not only the polar compounds such as quassin and neoquassin but also the non-polar substances, with the effect that the resulting gum was difficult to crystallize, despite repeated attempts by seeding with crystals of quassin/neoquassin. Further exploration using ethanol as an extracting solvent was attempted and this is described below.

With the method using an indirect method of sonication, the heartwood chips were not placed directly in the ultrasonic bath but in a glass flask which contained an organic solvent mixture as the extracting medium. Since the organic solvents were not in direct contact with the ultrasonic bath, the danger of a fire or explosion was removed. It was deemed desirable that a condenser with running tap water should be connected to the extracting flask. This served two purposes. Firstly, it prevented any flammable organic solvent escaping and so removed the danger of ignition of the solvents. In addition, since the ultrasonic bath does generate some heat, especially when it runs for a considerable period of time, the temperature of the mixture being sonicated can rise to near 60° C. At this temperature, in the conditions of the sonication, since mixtures of organic solvents are used, there is the possibility of evaporation of the more volatile solvents. This could result in a changing of the extracting solvent mixture over time during the sonication process. It could be observed that during the extraction, there is small amount of liquid being condensed and returned to the extracting flask.

It was found that the sonication time required for the complete extraction of the wood chips by either direct sonication of the wood chips in water, or by indirect sonication in an organic solvent were about the same.

The use of another organic solvent mixture attempted, that of 50%:50% ethanol in hexane, gave a most surprising result after indirect sonication. Off-white, crystals of quassin/neoquassin, fairly pure as indicated by tlc, were obtained and crystallization occurred directly in the flask upon evaporation of the solvent. This would represent one of the most simple and direct methods with which to obtain fairly pure crystals of quassin/neoquassin from the heartwood chips. Basically, this was achieved in one step by evaporation of the solvent after indirect sonication. The significance of such an extraction is that the normal steps of concentration, and isolation, by such methods as chromatography, would have now been unnecessary. A taste of the spent wood chips, however, indicated that after what was deemed a sufficient sonicating time to have extracted all of the quassin/neoquassin as would have been extracted with that solvent mixture, there was still some bitterness in the wood chips.

After trials of other solvent mixtures, it was found possible to extract the quassinoids from the heartwood chips quantatively, where the wood chips were completely bland to the taste indicating removal of all the quassinoids, and yet to obtain a gum still for which the tlc. indicated that it was rich in quassin and neoquassin, and in addition, one that could be induced to crystallize by seeding with crystals of quassin/neoquassin. This was achieved, e.g., with the use of a solvent mixture of 50% ethanol, 25% ethyl acetate, and 25% hexane. In effect, this meant that essentially in one step, one was able to extract the quassinoids from the heartwood chips with the resulting gum confirmed as richly containing quassin/neoquassin by tlc., and being sufficiently readily crystallizable by e.g. seeding. This method obviated the necessity of partitioning with ethyl acetate in order to extract the quassinoids from the sonicating solvent.

Optimization of the Process

With the extraction with ethanol, both polar and non-polar substances were extracted in the process. In an attempt to modify the extraction in a favorable manner, it was decided to extract the heartwood by indirect sonication, firstly with hexane. This would then be followed by sonication of the chips with ethanol. With this sequence of solvents, it was thought that the initial extraction with hexane would have removed the non-polar compounds and that the extraction in ethanol would then afford a gum, with primarily the quassinoids and so would be relatively pure and would be readily crystallizable.

In the process, it was found that hexane was a poor solvent for extraction with this method and although only non-polar substances were removed as indicated by the t.l.c, only a small quantity of an oily gum was extracted from the wood chips. With the subsequent extraction of the wood chips using the same method with ethanol, the ethanol once again extracted not only the polar compounds but a large quantity of the non-polar substances, which apparently had not been extracted by the hexane With this result, it was realized that the benefit of using a mixture of organic solvent to achieve the desired result of quantitative extraction of quassinoids and minimization of the impurities extracted. As mentioned above, one solvent mixture, that of 50:50 ethanol/hexane resulted in the extraction of a fairly pure readily crystallizable mixture of quassin/neoquassin. Subsequently, using a mixture of ethanol, 50%: ethyl acetate 25%; hexane 25%, it was possible to quantitatively remove all the quassinoids in a gum that was sufficiently pure by t.l.c. and sufficiently readily crystallizable by seeding into mixed crystals of quassin/neoquassin.

The Ultrasonic Bath used for the extractions was a Branson, Model 3510 Ultrasonic Bath with a capacity of 5.5 L. T.l.c's were developed on Silicycle, plastic backed TLC plates., with a mixture of EtOAc 60%, Hexane 39%, and Methanol 1%, as the eluting solvent. U.V. spectra were done with a Thermo Scientific Helios Omega UV-Vis Spectrometer, with acetonitrile as the solvent. The Bitterwood chips to be extracted were cut into small slivers of approx. size 25×3×2 mm.

Indirect Sonication of Bitterwood Chips in Ethanol

Bitterwood heartwood chips (25 g) were placed in a flask to which was added ethanol (300 mL) and the flask placed in the ultrasonic bath with water as the sonicating medium. After sonicating for approx. 40 hrs., it was noticed that the chips were quite bland to the taste indicating that most of the quassinoids contained therein had been extracted. Sonication was continued to a period of 50 hrs. after which the chips were now completely bland to the taste.

The ethanol was changed three times during the period of sonication to prevent any saturation of the extracting solvent and fresh ethanol added to the chips. The decanted ethanol was filtered and the solvent removed by evaporation to afford a gum (1.902 g). The t.l.c. indicated the presence of quassin/neoquassin but there were several non-polar impurities present. The gum could not be induced to crystallize, even with seeding with crystals of quassin/neoquassin.

Initial Indirect Sonication of the Wood Chips with Hexane

Bitterwood heartwood chips (25 g) were extracted in the manner described above with hexane (300 mL.). After 25 hrs, sonication, extraction appeared to have been complete, the extracting solvent appearing to be of a constant color.

The hexane was decanted once during the sonication process and fresh hexane was re-added as the extracting solvent. The woodchips were very bitter to the taste. The combined hexane fractions was bland to the taste indicating that no quassinoids were extracted and this was confirmed by t.l.c. Evaporation of the hexane gave an oily gum (0.1182 g).

Indirect Sonication of the Wood Chips Initially Extracted with Hexane, with Ethanol Bitterwood heartwood chips (25 g) after indirect sonication with hexane as described immediately above, were then extracted with ethanol (300 mL). Sonication was continued for a period of 50 hrs., after which the wood chips were completely bland to the taste. The sonicating ethanol was changed twice during the extraction process and fresh ethanol added to the sonicating flask. The ethanol fractions were filtered, combined and evaporated to leave a gum (2.0508 g), the t.l.c of which indicated the presence of primarily a mixture of quassin/neoquassin but with a fair amount of non-polar compounds. The gum could not be induced to crystallize despite seeding with crystals of quassin/neoquassin.

Indirect Sonication with a Solvent Mixture of Hexane 50% and Ethanol 50%

Bitterwood heartwood chips (25 g) were extracted by indirect sonication, in the method described above for 50 hrs. The extracting solvent mixture was decanted once and a fresh solvent mixture added after 26.4 hrs. into the process.

Evaporation of the solvent mixture resulted in an off-white crystalline mass (0.2804 g), the t.l.c. of which indicated that the crystalline mixture was a fairly pure crystalline mixture of quassin/neoquassin. The remaining wood chips were still bitter to the taste indicating that some quassinoids remained after the extraction process.

Indirect Sonication with a Solvent Mixture of Ethanol 50%, Ethyl Acetate 25%, Hexane 25%

Bitterwood heartwood chips (25 g) were extracted in the manner described above with a solvent mixture of Ethanol 50%, Ethyl Acetate 25%, and Hexane 25%. The sonication was conducted over a period of 53 hrs. with a change of solvent after 22 hrs. Filtration and evaporation of the solvent gave a gum (1.3919 g), the t.l.c. of which indicated that the mixture contained quassin/neoquassin. The gum crystallized upon seeding with crystals of quassin/neoquassin in ethanol.

The wood chips were completely bland to the taste indicating that all the quassinoids had been extracted. The t.l.c. of the extracted gum indicated that it contained a high concentration of quassin/neoquassin, it had the characteristic u.v. absorption curve for quassin at 255 nm.

Repeated Indirect Sonication with a Solvent Mixture of Ethanol 50%, Ethyl Acetate 25%, and Hexane 25%

Bitterwood heartwood chips (25 g) were extracted in the manner described above with the solvent mixture Ethanol 50%, Ethyl Acetate 25%, and Hexane 25% (300 mL).

The wood chips were sonicated for a total period of 55 hrs., with a change of the solvent mixture after 24 hrs., into the process and fresh solvent added to the extracting flask. The extracting solvent was filtered and evaporated to give a gum (1.4207 g) which crystallized after seeding with crystals of quassin/neoquassin and the t.l.c. of which indicated that it contained quassin/neoquassin. The wood chips were completely bland to the taste. The gum had the characteristic u.v. absorption curve of quassin at 255 nm.

Those skilled in the art would readily appreciate that all methods and examples described herein are meant to be exemplary and that actual methods and examples will depend upon the specific application for which the methods of the present invention are used. Those skilled in the art will recognize, or be able to ascertain using no more than routine experimentation, many equivalents to the specific embodiments of the invention described herein. It is, therefore, to be understood that the foregoing embodiments are presented by way of example only and that the invention may be practiced otherwise than as specifically described. Accordingly, those skilled in the art would recognize that the use of a method in the examples should not be limited as such. The present invention is directed to each individual method described herein. In addition, any combination of two or more such methods, if such methods are not mutually inconsistent, is included within the scope of the present invention.

We claim:

1. A method of extracting quassin and neoquassin from *Picrasma excelsea* by indirect sonication without organic phase/aqueous phase separation or column chromatography, the method comprising the steps of:
   (a) mixing a natural substance comprising bark and/or wood from a *Picrasma excelsea* plant with an organic solvent mixture comprising ethanol and hexane in a first container,
   (b) placing said first container into a second container containing water,
   (c) applying ultrasonic energy to the second container for a sufficient duration of time to result in a least 90% extraction of the quassin and neoquassin from the *Picrasma excelsea* into the organic solvent mixture,
   (d) removing the bark and/or wood from the organic solvent mixture to produce an organic phase containing the quassin and neoquassin,
   (e) evaporating the organic phase to produce a quassin and neoquassin residue, and
   (f) recrystallizing the residue to produce crystalline quassin and neoquassin.

2. The method of claim 1, wherein the organic solvent mixture further comprises ethyl acetate.

3. The method of claim 2, wherein ethyl acetate, hexane, and ethanol are in a 1:1:1, 1:2:1, 1:1:2, 2:1:1, 2:2:1, or 1:2:2 ratio by volume.

4. The method of claim 1, wherein the organic solvent mixture is a mixture of ethanol and hexane.

5. The method of claim 4, wherein ethanol and hexane are in a ratio by volume from about 1:2 to about 2:1.

6. The method of claim 1, wherein the natural substance consists essentially of the bark of the plant.

7. The method of claim 1, wherein the natural substance comprises about 11% of the bark and about 89% of the heartwood of the plant.

8. The method of claim 1, wherein the natural substance comprises the bark of the plant.

* * * * *

UNITED STATES PATENT AND TRADEMARK OFFICE
CERTIFICATE OF CORRECTION

| | | |
|---|---|---|
| PATENT NO. | : 10,570,110 B2 | Page 1 of 2 |
| APPLICATION NO. | : 13/955992 | |
| DATED | : February 25, 2020 | |
| INVENTOR(S) | : Trevor Herbert Yee et al. | |

It is certified that error appears in the above-identified patent and that said Letters Patent is hereby corrected as shown below:

In the Specification

At Column 3, Lines 44-46, should read:
In any of the preceding embodiments, the natural substance is *Picrasma excelsa, Picrasma quassioides, Quassia amara* or *Quassia africana.*

At Column 6, Lines 4-6, should read:
In any of the preceding embodiments, the method further includes: the natural substance is *Picrasma excelsa, Picrasma quassioides, Quassia amara* or *Quassia africana.*

At Column 9, Line 51-Column 10, Lines 1-2, should read:
A second embodiment of extracting quassinoids using a natural substance is described. In some embodiments, the natural substance includes a tree which is a plant of the plant family Simaroubaceae. In some embodiments, the tree includes *Picrasma excelsa, Picrasma quassioides, Quassia amara* or *Quassia africana.* The natural substance includes bark of the tree, heartwood of the tree, and a combination thereof. Any bark of a tree which contains quassinoids can be used as the natural substance for extracting quassinoids using methods disclosed herein. In some embodiments, the natural substance for extraction used contains a mixture of tree bark and wood chip in the naturally occurring ratio. The method comprises: (a) providing a first mixture of the natural substance with water, wherein the first mixture is free of organic solvent; (b) extracting the quassinoid at room temperature to provide a first aqueous phase containing quassinoid; and (c) extracting the quassinoid from the first aqueous phase with a first water-immiscible organic solvent to yield a first organic phase containing the quassinoid.

At Column 10, Lines 42-59, should read:
In some embodiments, quassinoid are extracted from bark of Bitterwood, *Picrasma excelsa,* using the method described in Figure 3. As shown in Figure 3, a natural substance including tree bark is subjected to sonication extraction using water as solvent at room temperature. Without being bound to any particular theory, it is believed that sonication improves the efficiency of the extraction and the use of low temperature and non-organic extraction solvent efficiently reduces the non-polar impurities.

Signed and Sealed this
Twenty-third Day of June, 2020

Andrei Iancu
*Director of the United States Patent and Trademark Office*

In some embodiments, the natural substance is a bark of a tree of the plant family Simaroubaceae. In some embodiments, the tree is *Picrasma excelsa, Picrasma quassioides. Quassia amara* or *Quassia africana.* In some embodiments, natural substance is a mixture of the bark and heartwood of the plant. In some embodiments, the mixture comprises about 11 wt% of the bark and about 89 wt% heartwood of the plant, which corresponds to the natural composition normally presented in the tree.

At Column 15, Lines 43-49, should read:
Any natural substance containing quassinoids may be used in the indirect sonication. The natural substance can be a plant of the plant family Simaroubaceae. In some embodiments, the natural substance used is *Picrasma excelsa, Picrasma quassioides, Quassia amara* or *Quassia africana.* As described herein, any portion of the plant, e.g., bark or heartwood, can be used in indirect sonication.

In the Claims

Claim number 1; in Column 22, Lines 22-42, should read:
1. A method of extracting quassin and neoquassin from *Picrasma excelsa,* by indirect sonication without organic phase/aqueous phase separation or column chromatography, the method comprising the steps of:
    (a) mixing a natural substance comprising bark and/or wood from a *Picrasma excelsa* plant with an organic solvent mixture comprising ethanol and hexane in a first container,
    (b) placing said first container into a second container containing water;
    (c) applying ultrasonic energy to the second container for a sufficient duration of time to result in at least 90% extraction of the quassin and neoquassin from the *Picrasma excelsa* into the organic solvent mixture,
    (d) removing the bark and/or wood from the organic solvent mixture to produce an organic phase containing the quassin and neoquassin,
    (e) evaporating the organic phase to produce a quassin and neoquassin residue, and
    (f) recrystallizing the residue to produce crystalline quassin and neoquassin.